(12) United States Patent
Eder et al.

(10) Patent No.: US 6,299,627 B1
(45) Date of Patent: *Oct. 9, 2001

(54) WATER-SOLUBLE COATING FOR BIOACTIVE VASOOCCLUSIVE DEVICES

(75) Inventors: Joseph C. Eder, Los Altos Hills, CA (US); Stanley W. Olsen, Jr., Dallas, TX (US); Paul C. Slaikeu, Hayward; Robert M Abrams, Sunnyvale, both of CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/414,616

(22) Filed: Oct. 8, 1999

Related U.S. Application Data

(63) Continuation of application No. 09/100,426, filed on Jun. 18, 1998, now Pat. No. 5,980,550.

(51) Int. Cl.⁷ .................................................. A61M 29/00
(52) U.S. Cl. .................................................. 606/191
(58) Field of Search .................................... 606/190, 191, 606/192, 207, 108; 623/1

(56) References Cited

U.S. PATENT DOCUMENTS

| | | |
|---|---|---|
| 3,847,652 | 11/1974 | Fletcher et al. . |
| 4,739,768 | 4/1988 | Engleson . |
| 4,994,069 | 2/1991 | Ritchart et al. . |
| 5,122,136 | 6/1992 | Guglielmi et al. . |
| 5,147,370 | 9/1992 | McNamara et al. . |
| 5,226,911 * | 7/1993 | Chee et al. .......................... 606/191 |
| 5,234,437 * | 8/1993 | Sepetka ............................... 606/108 |
| 5,250,071 | 10/1993 | Palermo . |
| 5,261,916 | 11/1993 | Engelson . |
| 5,304,194 | 4/1994 | Chee et al. . |
| 5,304,195 | 4/1994 | Twyford, Jr. et al. . |
| 5,312,415 | 5/1994 | Palermo . |
| 5,350,397 | 9/1994 | Palermo et al. . |
| 5,354,295 | 10/1994 | Guglielmi et al. . |
| 5,380,299 * | 1/1995 | Fearnot et al. ......................... 623/1 |
| 5,382,259 | 1/1995 | Phelps et al. . |
| 5,383,928 | 1/1995 | Scott et al. . |
| 5,527,338 | 6/1996 | Purdy . |
| 5,536,274 | 7/1996 | Neuss . |
| 5,624,411 * | 4/1997 | Tuch ................................... 604/265 |
| 5,624,461 | 4/1997 | Mariant . |
| 5,639,277 | 6/1997 | Mariant et al. . |
| 5,643,580 * | 7/1997 | Subramaniam .................... 424/400 |
| 5,645,082 | 7/1997 | Sung et al. . |
| 5,645,558 | 7/1997 | Horton . |
| 5,649,949 | 7/1997 | Wallace et al. . |
| 5,658,308 * | 8/1997 | Snyder ................................ 606/191 |
| 5,669,931 | 9/1997 | Kupiecki et al. . |
| 5,690,671 | 11/1997 | McGurk et al. . |
| 5,700,286 | 12/1997 | Tartaglia et al. . |
| 5,733,294 | 3/1998 | Forber et al. . |
| 5,749,894 | 5/1998 | Engleson . |
| 5,792,154 | 8/1998 | Doan et al. . |
| 5,980,550 * | 11/1999 | Eder et al. ............................ 606/191 |

FOREIGN PATENT DOCUMENTS

| | | |
|---|---|---|
| 196 46 280 | 10/1997 | (DE) . |
| WO 94/10936 | 5/1994 | (WO) . |
| WO 98/04315 | 2/1998 | (WO) . |

* cited by examiner

Primary Examiner—Henry J. Recla
Assistant Examiner—Tan-Uyen T. Ho
(74) Attorney, Agent, or Firm—Morrison & Foerster LLP

(57) ABSTRACT

A vaso-occlusive device having an inner coating and a water-soluble outer coating. Methods of preparing the devices are also provided.

13 Claims, 1 Drawing Sheet

WATER-SOLUBLE COATING FOR BIOACTIVE VASOOCCLUSIVE DEVICES

This application is a continuation of U.S. application Ser. No. 09/100,426, filed Jun. 18, 1998, now U.S. Pat. No. 5,980,550.

FIELD OF THE INVENTION

This invention relates to a medical device for forming an embolism within the vasculature of a patient. More particularly, it concerns an occlusion device having an outer coating of a dissolvable, water-soluble agent over an inner coating.

BACKGROUND

Vaso-occlusive devices are surgical implements that are placed within open sites in the vasculature of the human body. The devices are introduced typically via a catheter to the site within the vasculature that is to be closed. That site may be within the lumen of a blood vessel or perhaps within an aneurysm stemming from a blood vessel.

There are a variety of materials and devices which have been used to create such emboli. For instance, injectable fluids such as microfibrillar collagen, various polymeric foams and beads have also been used. Polymeric resins, particularly cyanoacrylate resins, have been used as injectable vaso-occlusive materials. Both the injectable gel and resin materials are typically mixed with a radio-opaque material to allow accurate siting of the resulted material. There are significant risks involved in use of a cyanoacrylates, because of the potential for misplacement. Such a misplacement would create emboli in undesired areas. Cyanoacrylate resins or glues are somewhat difficult, if not impossible, to retrieve once they are improperly placed.

Other available vaso-occlusive devices include mechanical vaso-occlusive devices. Examples of such devices are helically wound coils and braids. Various shaped coils have been described. For example, U.S. Pat. No. 5,624,461 to Mariant describes a three-dimensional in-filling vaso-occlusive coil. U.S. Pat. No. 5,639,277 to Mariant et al. describe embolic coils having twisted helical shapes and U.S. Pat. No. 5,649,949 to Wallace et al. describes variable cross-section conical vaso-occlusive coils. A random shape is described, as well. U.S. Pat. No. 5,648,082 to Sung et al., describes methods for treating arrhythmia using coils which assume random configurations upon deployment from a catheter. U.S. Pat. No. 5,537,338 to describes a multi-element intravascular occlusion device in which shaped coils may be employed. Spherical shaped occlusive devices are described in U.S. Pat. No. 5,645,558 to Horton. Horton describes how one or more strands can be wound to form a substantially hollow spherical or ovoid shape when deployed in a vessel. U.S. patent application Ser. No. 07/978,320, filed Nov. 18, 1992, entitled "Ultrasoft Embolization Coils with Fluid-Like Properties" by Berenstein et al., is found a coil having little or no shape after introduction into the vascular space.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximately extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

In addition, several patents describe deployable vaso-occlusive devices that have added materials designed to increase their thrombogenicity. For example, fibered vaso-occlusive devices have been described at a variety of patents assigned to Target Therapeutics, Inc., of Fremont, Calif. Such vaso-occlusive coils having attached fibers is shown in U.S. Pat. Nos. 5,226,911 and 5,304,194, both to Chee et al. Another vaso-occlusive coil having attached fibrous materials is found in U.S. Pat. No. 5,382,259, to Phelps et al. The Phelps et al. patent describes a vaso-occlusive coil which is covered with a polymeric fibrous braid on its exterior surface. U.S. Pat. No. 5,658,308 to Snyder is directed to a coil having a bioactive core.

In other attempts to increase thrombogenesis, vaso-occlusive coils have also been treated with variety of substances. For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. The coils may be coated with agarose, collagen or sugar.

U.S. Pat. No. 5,669,931 to Kupiecki discloses coils that may be filed or coated with thrombotic or medicinal material. U.S. Pat. No. 5,749,894 to Engleson discloses polymer coated vaso-occlusion devices. U.S. Pat. No. 5,690,671 to McGurk discloses an embolic element which may include a coating, such as collagen, on the filament surface.

U.S. Pat. No. 5,536,274 to Neuss shows a spiral implant which may assume a variety of secondary shapes. Some complex shapes can be formed by interconnecting two or more of the spiral-shaped implants. To promote blood coagulation, the implants may be coated with metal particles, silicone, PTFE, rubber latices, or polymers.

None of the above documents address the complications of deploying devices with a bioactive coating, such as one which increases thrombogenicity. Of the patents which disclose implantable stents which are treated so as to retard deposition of unwanted materials (see e.g., U.S. Pat. No. 5,147,370 to McNamara et al. and U.S. Pat. No. 5,383,928 to Scott et al.), the treated devices are not vaso-occlusive coils and, in addition, these anti-thrombotic components are generally permanently bound to the stents.

In addition, these devices do not contain an inner, bioactive coating which is generally permanently bonded or attached to the device. Although these bioactive coatings provide therapeutics or increase thrombogenicity of vaso-occlusive devices in vivo, the inner coating may induce complications during coil packing and coil manipulation. None of the documents discussed above make any suggestion of treating vaso-occlusive coils with a dissolvable outer coating over a bioactive inner coating.

SUMMARY OF THE INVENTION

In one aspect, the present invention provides a vaso-occlusive device comprising: a) a biocompatible metal vaso-occlusive member; b) an inner bioactive coating on said vaso-occlusive member; and c) an outer coating on said inner coating, said outer comprising a water-soluble agent. The vaso-occlusive member may be a coil, a sphere, or other shaped structure. In one preferred embodiment, the vaso-occlusive member is an elongated helical coil comprises of a series of axial windings, for instance a cylindrical helical coil. Preferably, the coil is made of gold, rhenium, platinum, palladium, rhodium, ruthenium, stainless steel, tungsten and alloys thereof.

The inner bioactive coating may be any active substance, for example, a thrombogenic agent that promotes healing, or another therapeutic agent. Preferably, the inner coating is permanently bonded to said vaso-occlusive member. The inner coating can be collagen, fibrinogen, growth factors and synthetic peptides. The inner coating may also be deposited on the member by plasma treatment.

The dissolvable outer coating can be an anti-thrombogenic agent, a therapeutic agent or an agent which reduces friction during delivery. In one preferred embodiment, the outer coating is acetyl salicylic acid (aspirin), heparin, tissue plasminogen activator (TPA), streptokinase, urokinase, hiridun, coumadin or alnert. In yet another embodiment, the outer coating further includes a component that affects the solubility of said outer coating. This component can be made part of the outer coating before deposition on the member or, alternatively, can be deposited as an overcoating over the outer coating. In one preferred embodiment, the water-soluble, anti-thrombotic outer coating dissolves shortly after said vaso-occlusive member is deployed. Preferably, the inner and outer coatings do not affect the shape of said vaso-occlusive member after deployment.

In another aspect, the invention provides a method for treating a vaso-occlusive device comprising (a) providing an inner coating for a vaso-occlusive device comprising a bioactive material; and (b) providing an outer coating over said inner coating, said outer coating comprising a dissolvable water-soluble material. In one embodiment, the vaso-occlusive device comprises a metallic element, for instance a helically wound coil. The coil may be made from gold, rhenium, platinum, palladium, rhodium, ruthenium, stainless steel, tungsten and alloys thereof.

Preferably, the inner coating is thrombogenic and is permanently bonded to the vaso-occlusive member and may be collagen, fibrinogen, vitronectin, a growth factor or a synthetic peptide. The inner coating may also be created by plasma treatment of the vaso-occlusive member. The outer coating is preferably anti-thrombogenic, for example, acetyl salicylic acid (aspirin), heparin, coumadin or alnert. Optionally, the outer coating contains a component such as a lipid (phosphatidyl choline) or hydrophilic compound (e.g., polyvinyl alcohol). The optional component may affect the rate at which the outer coating dissolves.

In yet another aspect, the present invention provides a produced by the methods described herein.

As will become apparent, preferred features and characteristics of one aspect of the invention are applicable to any other aspect of the invention.

MODES FOR CARRYING OUT THE INVENTION

The present invention provides a vaso-occlusive device having an outer coating of dissolvable, water-soluble agent. This dissolvable agent performs "temporary" functions, for example when the coating is an anti-thrombogenic agent, it reduces the likelihood of thrombus formation on the vaso-occlusive device or in the aneurysm during the delivery process. Other suitable water-soluble outer coatings include agents which reduce friction or pharmaceutic agents.

In one aspect, the outer, anti-thrombotic coating is placed over an inner coating of a bioactive agent. The term "bioactive" refers to any agent which exhibits effects in vivo, for example an thrombotic agent, a therapeutic agent or the like. The terms "thrombotic" and "thrombogenicity" are used to refer to any substance which increases or promotes adhesion of any of the components of blood and/or plasma, including but not limited to, blood cells, platelets, and other blood-borne components. Preferably, the inner coating is permanently bonded to the coil, while the outer coating is designed to dissolve shortly after coil deployment so that the underlying material can safely perform its intended purpose, i.e. being the healing cascade within the vessel. The outer coating may be water soluble, anti-thrombotic, anticoagulant or antiplatelet material of any type. The outer coating may be dip or spray coated, wiped onto the coil or attached by other means such as vapor deposition. Other methods will be known to those in the art.

Figure 1:
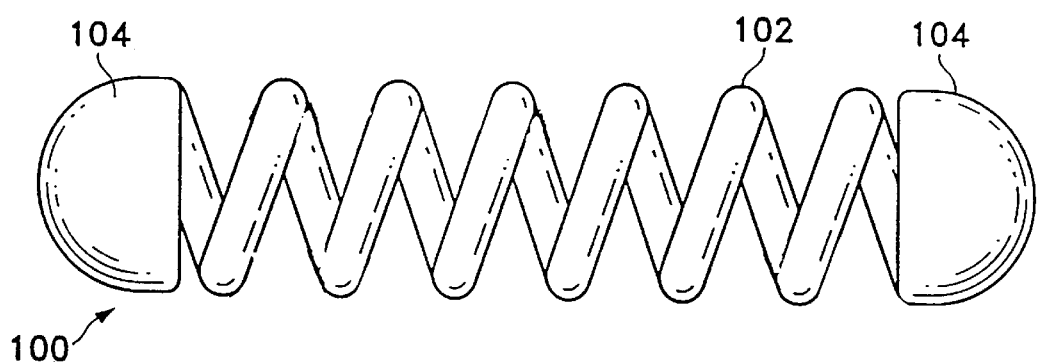
FIG. 1 is a perspective view of one embodiment of the invention.
Figure 2:
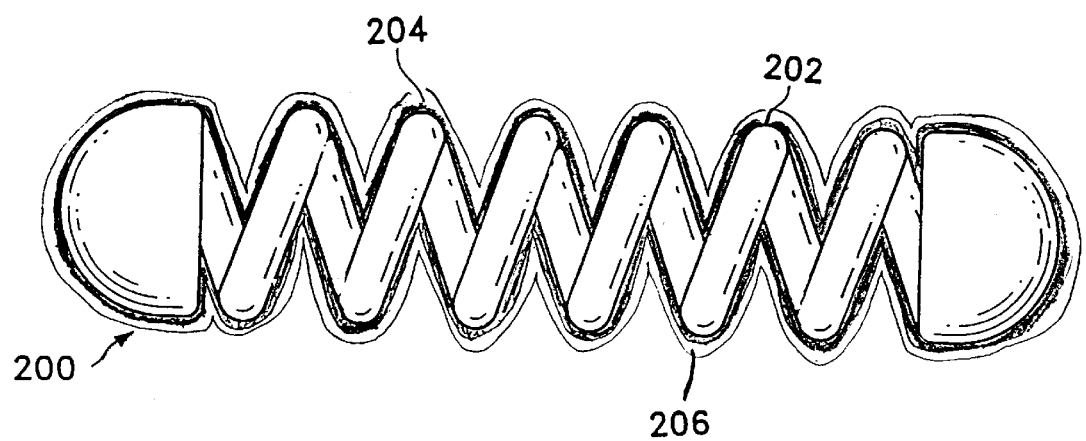
FIG. 2 is a perspective view of another embodiment of the invention showing a coil having a permanently bonded inner coating and a water-soluble, dissolvable outer coating.

FIGS. 1 and 2 show typical vaso-occlusive devices suitable for use with this procedure. FIG. 1 shows a typical vaso-occlusive device (100). Vaso-occlusive device (100) is shown in FIG. 1 to comprise a helically wound coil (102) having tips (104) to ease the potential of the component wire to cause trauma in a blood vessel. The device may include tufts or fiber bundles attached to it, so to increase the amount and volume of fiber held by the coil and thereby to promote overall thrombogenicity of the device. Typical of a vaso-occlusive device comprising a helical coil having attached fibrous elements such as shown in FIG. 1 is found in U.S. Pat. No. 5,226,911 to Chee et al, the entirety of which is incorporated by reference.

FIG. 2 shows a vaso-occlusive device (200) comprising a helically wound coil (202), an inner coating (204) and an outer coating (206). The inner coating is generally a substance which is permanently bound to the coil (202) and which increase thrombogenicity of the coil.

The occlusion devices of the invention may be made using conventional equipment and procedures. For example, helical coils may be prepared by wrapping a suitable wire about a cylindrical or conical mandrel. The strand(s) are then placed axially through the core of the helix and, if a multiplicity of strands are employed, their ends bound by heat, adhesives, or mechanical means. Radial filaments may be attached to the windings of the helix by tying or with adhesives.

The polymeric materials used in the vaso-occlusive devices in FIG. 1 and FIG. 2 are known materials. They are those materials which are generally approved for use as implants in the body or could be so approved. They may be of polymers such as polyethylene, polyacrylics, polypropylene, polyvinylchloride, polyamides such as Nylon, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and the like. When the polymers are fibrous, they are often looped or tufted as shown in the drawings. Although it is not critical to this invention, they are usually assembled in bundles of 5 to 100 fibers per bundle. Preferred materials for the polymer component of vaso-occlusive devices comprise polyesters, polyethers, polyamides, and polyfluorocarbons. Especially preferred is polyethyleneterephthalate, sold as Dacron.

The coils (102 in FIG. 1 and 202 in FIG. 2) may be made of any of a wide variety of biocompatible metals. In particular, the metals may be selected from gold, rhenium, platinum, palladium, rhodium, ruthenium, various stainless steels, tungsten, and alloys thereof. The preferred alloy is one comprising upwards of 90 percent platinum and at least a portion of the remainder, tungsten. This alloy exhibits excellent biocompatibility and yet has sufficient strength and ductility to be wound into coils of primary and secondary shape and will retain those shapes upon placement of the vaso-occlusive device in the human body. The diameter of the wire typically making up the coils is often in a range of 0.005 and 0.050 inches. The resulting primary coil diameter typically is in the range of 0.008 and 0.085 inches. Smaller coil diameters are used for finer problems and larger coil diameters and wire diameters are used in larger openings in the human body. A typical coil primary diameter is 0.015 and 0.018 inches. The axial length of a vaso-occlusive device may be between 0.5 and 100 centimeters. The coils are typically wound to have between 10 and 75 turns per centimeter.

In addition to the coils shown in the Figures, the vaso-occlusive device may comprise a substrate comprising a woven braid rather than the helical coil shown in those Figures. The vaso-occlusive device may comprise a mixture of coil and braid. Indeed, it is within the scope of this invention that a portion of the coil be polymeric, be a double winding mixture of metal and polymer, but in any event the vaso-occlusive device treated by a procedure of this invention must comprise a polymeric (natural or synthetic) fiber.

It is further within the scope of this invention that the vaso-occlusive device comprise shapes or structures other than coils or braids, for examples, solid sphere structures and the like.

In one aspect of the present invention, the vaso-occlusive devices described above and those similar to those specifically described above, are first treated with a coating of a bioactive coating and then subjected to treatment to provide a water-soluble material. Preferably, neither the inner nor outer coatings interfere with the shape of the coil after deployment.

The outer coating may have one or more functions, including, but not limited to, reducing friction, providing a therapeutic for local or blood borne delivery, or reducing thrombosis, coagulation or platelet activity. Examples of suitable hydrophilic compounds include polyvinyl alcohol (PVA), polyvinylpyrrolidone (PVP), polyacrylamide and the like. Hydrophobic compounds include membrane lipids such as phosphatidyl choline, fatty acid esters and the like. Examples of water soluble therapeutics include thrombolytics such as tissue plasminogen activator (TPA), streptokinase, urokinase, hirudin and growth factors such as vEGF. Particularly preferred materials for anti-thrombogenic outer coatings include, but are not limited to, acetyl salicylic acid (aspirin), heparin, coumadin, alnert, along with esters or other derivatives of these compounds. The outer coating is designed to perform a temporary function, preferably during and immediately after delivery of the device. For example, an anti-thrombogenic outer coating reduces thrombus formation on the coil during delivery.

The outer coating preferably dissolves shortly after deployment of the device. The rate of dissolution may be controlled by using chemical bonding of various degrees to the substrate layer, or alternatively, by the addition of a third component which affects solubility. For example, hydrophilic substances such as polyvinyl alcohol or lipids such as phosphatidyl choline.

Treatment of vaso-occlusive coils with a water-soluble material can be carried out by any means known in the art, for example dip coating, spray coating, wiping, vapor deposition or the like.

The rate of dissolution of the outer coating may be controlled by using chemical bonding of various degrees to the substrate layer or by the addition of a third component that would affect the solubility of the outer layer. Non-limiting examples of these substances include hydrophilic compounds such as polyvinyl alcohol and lipids such as phosphatidyl choline. The solubility-affecting substances can be added as an overcoating after the outer coating has been deposited on the coil or mixed into the outer coating before it is coated onto the vaso-occlusive device.

The inner, or bioactive coating or material is generally permanently bonded or attached to the coil. Preferably, the inner coating promotes cell attachment, more preferably it is thrombogenic. Non-limiting examples of bioactive coatings or materials which increase cell attachment and/or thrombogenicity include both natural and synthetic compounds, e.g., collagen, fibrinogen, vitronectin, other plasma proteins, growth factors (e.g., vascular endothelial growth factor, "vEGF"), synthetic peptides of these and other proteins having attached RGD (arginine-glycine-aspartic acid) residues, generally at one or both termini.

Another suitable thrombogenic bioactive coating involves "plasma treatment" of coils. (See, e.g., co-pending U.S. Ser. No. 08/598,325). These plasma-treated coils exhibit an amino-functionality which may be measured using known chemical methods. When the devices treated by this process are placed in a bloodstream, the amino-functionality results in a slight positive ionic charge on the surface of the fibers. This amino-functionality attracts platelets and thrombogenic proteins from the bloodstream. Plasma treatment may be carried out using e.g., a plasma generator such as that found in U.S. Pat. No. 3,847,652. The plasma may comprise a nitrogen containing gas, preferably those containing diatomic nitrogen or ammonia. Gas pressures are advantageously maintained at a very low level, e.g., no greater than about 5 millimeters of mercury, preferably from 0.1 to 2 millimeters of mercury.

The period of time in which the vaso-occlusive device is subjected to the plasma need not be great. That is to say that for most applied power settings below about 200 watts and in the radio frequency region between 1 and 50 megahertz, the time of reaction need not be greater than 10 minutes to achieve the result described herein.

Other suitable bioactive inner coatings include therapeutic agents which act locally and/or are distributed in vivo by blood flow.

The devices which are treated according to the procedure of this invention are often introduced to a selected site using the procedure outlined below. This procedure may be used in treating a variety of maladies. For instance, in treatment of an aneurysm, the aneurysm itself may be filled with the devices made according to the procedure specified here. Shortly after the devices are placed within the aneurysm, the outer coating dissolves, exposing the treated or untreated coil. An emboli begins to form and, at some later time, is at least partially replaced by collagenous material formed around the vaso-occlusive devices.

In general, a selected site is reached through the vascular system using a collection of specifically chosen catheters and guide wires. It is clear that should the aneurysm be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter as a unit. Once the tip of the guidewire reaches the end of the guiding catheter, it is then extended using fluoroscopy, by the physician to the site to be treated using the vaso-occlusive devices of this invention. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the mouth of an aneurysm to be treated, the guidewire is then withdrawn. The neurovascular catheter then has an open lumen to the outside of the body. The devices of this invention are then pushed through the lumen to the treatment site. They are held in place variously because of their shape, size, or volume. These concepts are described in the Ritchart et al patent as well as others. Once the vaso-occlusive devices are situated in the vascular site, the embolism forms.

Modifications of the procedure and device described above, and the methods of using them in keeping with this invention will be apparent to those having skill in this mechanical and surgical art. These variations are intended to be within the scope of the claims that follow.

What is claimed is:

1. A vaso-occlusive device comprising:
   a) a vaso-occlusive member;
   b) an inner coating on said vaso-occlusive member; and
   c) an outer coating on said inner coating, said outer coating comprising a water-soluble agent and a hydrophilic component that affects the solubility of said outer coating.

2. The device of claim 1, wherein the vaso-occlusive member is a metallic element comprising an elongated helical coil.

3. The device of claim 2 wherein the coil is a cylindrical helical coil.

4. The device of claim 2 wherein the coil comprises a metal selected from gold, rhenium, platinum, palladium, rhodium, ruthenium, stainless steel, tungsten and alloys thereof.

5. The device of claim 1 wherein the inner coating is permanently bonded to said vaso-occlusive member.

6. The device of claim 1 wherein the inner coating is created by plasma treatment.

7. The device of claim 1 wherein said outer coating is a water-soluble anti-thrombogenic agent.

8. The device of claim 1 wherein the outer coating is selected from the group consisting of acetyl salicylic acid, heparin, coumadin and alnert.

9. The device of claim 1 wherein said hydrophilic component is incorporated in the outer coating.

10. The device of claim 1 wherein said hydrophilic component is added as an overcoating on said outer coating.

11. The device of claim 1 wherein the water-soluble agent dissolves shortly after said vaso-occlusive member is deployed.

12. The device of claim 1 wherein the inner and outer coatings do not affect the shape of said vaso-occlusive member after deployment.

13. An implantable device for use in medical applications comprising:
   a) a support member;
   b) an inner coating on said support member; and
   c) an outer coating on said inner coating, said outer coating comprising a water-soluble agent and a lipid compound that affects the solubility of said outer coating.

* * * * *

UNITED STATES PATENT AND TRADEMARK OFFICE
CERTIFICATE OF CORRECTION

PATENT NO. : 6,299,627 B1
DATED : October 9, 2001
INVENTOR(S) : Joseph C. Eder, Stanley W. Olsen, Jr., Paul C. Slaikeu and Robert M. Abrams It is certified that error appears in the above-identified patent and that said Letters Patent is hereby corrected as shown below:

<u>Title page,</u>
Item [75] Inventors, change "Olsen" to -- Olson --.

Signed and Sealed this

Twenty-first Day of May, 2002

Attest:

JAMES E. ROGAN
*Director of the United States Patent and Trademark Office*

*Attesting Officer*